United States Patent [19]

Philippbar et al.

[11] Patent Number: 4,715,372

[45] Date of Patent: Dec. 29, 1987

[54] GAS INSUFFLATION APPARATUS FOR USE WITH AN ARTHROSCOPIC LASER SYSTEM

[76] Inventors: Jay E. Philippbar, 17931 Skypark Cir., Suite E, Irvine, Calif. 92714; Chadwick F. Smith, 1127 Wilshire Blvd., Los Angeles, Calif. 90017; Leroy V. Sutter, Jr., 17931 Skypark Cir., Suite E, Irvine, Calif. 92714

[21] Appl. No.: 743,939

[22] Filed: Jun. 12, 1985

[51] Int. Cl.$^4$ .............................................. A61B 17/36
[52] U.S. Cl. ................................................. 128/303.1
[58] Field of Search ........................................ 128/4–8, 128/204.23, 303.1, 395–398

[56] References Cited

U.S. PATENT DOCUMENTS

| | | | |
|---|---|---|---|
| 3,613,689 | 10/1971 | Crump | 128/303.1 |
| 3,823,575 | 7/1974 | Parel | 128/303.1 |
| 4,207,887 | 6/1980 | Hiltebrandt et al. | 128/204.23 |
| 4,292,973 | 10/1981 | Yamauchi et al. | 128/303.1 |
| 4,469,098 | 9/1984 | Davi | 128/303.1 |
| 4,550,240 | 10/1985 | Toida et al. | 128/303.1 |

FOREIGN PATENT DOCUMENTS 1159574  6/1963  Fed. Rep. of Germany ... 128/303.1

Primary Examiner—William E. Kamm
Assistant Examiner—Max F. Hindenburg

[57] ABSTRACT

The present invention is a gas insufflation apparatus which is used with an arthroscopic attachment having a gas inlet. A cylinder contains gas at a high pressure. A single stage regulator is fluidly coupled to the cylinder in order to regulate the inlet pressure of the gas. The gas insufflation apparatus includes a filter, an inlet relief valve and an inlet pressure gauge. The filter is fluidly coupled to the single stage regulator. The inlet relief valve insures that the inlet pressure of the gas does not exceed a predetermined pressure. The inlet pressure gauge reads the inlet pressure. The gas insufflation apparatus also includes a control valve and a flow meter. The control valve turns the flow of the gas through the gas insufflation apparatus on and off. The flow meter measures the flow of the gas through the gas insufflation apparatus. The gas insufflation apparatus further includes a first regulator and a second regulator. The first regulator insufflates the gas directly into the knee joint at a first preselected pressure in order to distend the knee joint during arthroscopic surgery. The second regulator insufflates the gas directly into the arthroscopic attachment through the gas inlet at a second preselected pressure which is slightly higher than the first preselected pressure in order to distend the knee joint and provide positive gas flow through the arthroscopic attachment during arthroscopic surgery by the laser system.

1 Claim, 2 Drawing Figures

GAS INSUFFLATION APPARATUS FOR USE WITH AN ARTHROSCOPIC LASER SYSTEM

BACKGROUND OF THE INVENTION

1. Field of the Invention

The present invention relates to a gas insufflation apparatus and more particularly to a gas insufflation apparatus which is used with an arthroscopic attachment of a hand-held $CO_2$ laser system arthroscopic attachment in order to distend a knee joint during arthroscopic surgery.

2. Description of the Prior Art

In their article, entitled "Laser Energy in Arthroscopic Meniscectomy," published in *Orthopedics*, Volume 6, Number 9, pages 1165-1169, Sept., 1983, Terry L. Whipple, Richard B. Caspari and John F. Meyers discussed the rationale and technique for performing arthroscopic meniscectomy with a carbon dioxide laser. They distended the knee joint with either nitrogen or carbon dioxide through the sleeve of the arthroscope via a gas infusion pump, which maintained the intraarticular pressure in the range of 80 to 100 mm Hg. Before they introduced the laser cannula through a separate portion, they switched the gas infusion to the laser cannula in order to prevent particulate or liquid from entering the laser cannula.

U.S. Pat. No. 4,369,768, entitled Arthroscope, issued to Marko Vukovic on Jan. 25, 1983, teaches an arthroscope.

On Oct. 11, 1983 Chadwick F. Smith and Leroy V. Sutter, Jr. filed an application, entitled An Arthroscopic Introducer for Use with a Laser System, having Ser. No. 540,298, described an arthroscopic introducer. A laser system is optically and mechanically coupled to the arthroscopic introducer so that the arthroscopic introducer may be used surgically under arthroscopic control. The arthroscopic introducer includes a gas inlet for letting a gas into the arthroscopic introducer and a lens focusing system for focusing the beam of light energy into an optical nozzle which functions as a high pressure gas nozzle.

In their article, entitled "The Use of Laser Beams for Operations in Haemophilia," published in *The Scandinavian Journal of Haemotology* in 1984, Supplementum 40, Volume 33, pages 281-289, 1984 F. Hefti, E. Morscher and F. Koller used a Sharplan 791 $CO_2$ Surgical Laser to perform five synovectomies of the knee joint, four synovectomies of the elbow joint and one splitting of the retinaculum of the knee joint.

U.S. Pat. No. 3,865,113, entitled Laser Device Particularly Useful as Surgical Scalpel, issued to Uzi Sharon and Isaac Kaplan on Feb. 11, 1975, teaches a laser beam manipulator including a tube which is optically coupled through an articulated arm to a $CO_2$ laser system and beam targeting member which is carried by the tube.

U.S. Pat. No. 3,710,798, entitled Laser System for Microsurgery, issued to Herbert C. Bredemeier on Jan. 16, 1973, teaches a laser system for microsurgery which includes a mirror for changing the direction of a beam of light energy from a $CO_2$ laser system and directing the beam to the treatment site.

U.S. Pat. No. 3,982,541, entitled Eye Surgical Instrument, issued to Francis A. L'Esperance on Sept. 28, 1976, teaches a method of surgically removing body tissue which includes the steps of contacting the body tissue with a probe open at a free end, passing a $CO_2$ laser beam through a central passage in the probe and the open end to the tissue at a power level sufficent to affect vaporization of tissue, vaporizing only the surface portion of the tissue exposed to the $CO_2$ laser beam in a manner so that the vaporizing step is surface phenomena at a depth not more than about 0.33 millimeters, introducing a gas stream into the probe downstream from the lenses associated with the $CO_2$ laser beam, passing the gas stream through the probe in a direction towards the free end of the probe and out of the probe, and removing smoke and any vaporized portion of the tissue through the probe by way of the gas stream.

U.S. Pat. No. 3,982,533, entitled Insufflation Apparatus, issued to F. M. Wiest on Sept. 28, 1976, teaches an apparatus for introducing limited quantities of carbon dioxide into the human body for operational purposes, particularly laparoscopy. The insufflation apparatus includes a control device for delivering the carbon dioxide, a connecting nipple on the control device for connecting a first flexible tubing to a first operative cannula of a dual Veress needle introducable into the body and a pressure gauge for indicating the pressure present in the body cavity. The insufflation apparatus also includes a second connection nipple which is disposed on the control device and which is connected by a nipple to a pressure gauge. The second connection nipple is connected by a second flexible tubing to a second coaxial cannula of the dual Veress needle so that the pressure gauge is directly connected with the body cavity rather through the first cannula of the dual Veress needle.

U.S. Pat. No. 4,048,992, entitled Insufflator, issued to Hans-Joachin Lindemann and F. M. Wiest on Sept. 20, 1977, teaches an apparatus for introducing limited quantities of carbon dioxide into the human body for operational purposes, particularly laparoscopy or hysteroscopy. The insufflation apparatus includes two pressure reducers, in series, followed by a gas flow monitoring device through which carbon dioxide is directed from a gas supply to a human body. The two pressure reducers are constantly adjusted to fixed gas supply pressures. The gas flow monitoring device includes a cylindrical expansion container which has a central inlet port and a large diameter, and in whose peripheral zone the gas flow velocity approaches a zero rate. First and second sensing elements for the measured variable are provided in the expansion container. The first sensing element is located immediately in the area of the inlet port and the second sensing element is located close to the cylindrical side wall at the maximum possible radial spacing from the first sensing element. The two sensing elements are included in a measuring bridge and a measuring amplifier is connected to the bridge output. An indicator of the rate of flow is connected to the amplifier output. The second pressure reducer may be adjusted to a supply pressure in the range of 15 to 200 mm Hg.

U.S. Pat. No. 4,207,887, entitled Gas Insufflation Apparatus, issued to Siegfried Hiltebrandt and Helmut Wurster on July 17, 1980, teaches a gas insufflation apparatus which introduces limited quantities of carbon dioxide into a body cavity for operational purposes, particularly laparoscopy or hysteroscopy. The gas insufflation apparatus includes a compressed gas cylinder containing carbon dioxide, the pressure of which is controlled and monitored by a first pressure gauge and a first pressure regulator in series. From the first pressure regulator the gas flows at reduced pressure via a shut-off valve to an intermediate container the pressure and quantity of gas in which can be read off a second pressure gauge. The container also has a safety valve. The reduced-pressure insufflation gas from the container flows through a second pressure regulator which is advantageously continuously adjustable and by means of which the desired gas pressure in a body cavity required by a particular patient can be preselected. The regulated pressure can be monitored by a third pressure gauge. To inject a volume of gas into the body cavity, a valve downstream of the second pressure regulator is opened manually so that the gas will then flow to the body cavity via a rate of flow controller, an insufflation duct and a tube constituted by the cannula. The preselected pressure is maintained by the second pressure regulator.

U.S. Pat. No. 3,709,214, entitled Gas Orburating Method, issued to Jack R. Robertson on Jan. 9, 1973, teaches a method of diagnosis and/or therapy of an internal part of the body which accessible from an adjacent body opening which includes the step introducing a gas under pressure.

U.S. Pat. No. 4,550,240, entitled Laser Irradiating Apparatus, issued to Masahiro Toida and Norihiro Suenaga and Nobuyuki Suenaga on Oct. 29, 1985, teaches a laser irradiating apparatus which includes first and second light guides for two laser beams at a first wavelength and a second wavelength, respectively, and first and second supply for a first assist gas and a second assist gas.

U.S. Pat. No. 3,885,590, entitled Gas Transmission and Monitoring Device, entitled to John L. Ford on May 27, 1975, teaches a compact self-contained flow and pressure regulator device which transmits and monitors gas from a source of compressed gas to a body cavity during surgery. The device includes a selectively adjustable pressure regulator which controls the gas received from the compressed gas source, a limiting orifice to attenuate the flow rate and an off-on valve. The device also includes an adjustable pressure valve which controls the discharge gas pressure, a gauge which indicates the discharge gas pressure, and a safety relief valve.

SUMMARY OF THE INVENTION

In view of the foregoing factors and conditions which are characteristic of the prior art it is the primary object of the present invention to provide a gas insufflation apparatus for use with an arthroscopic attachment of the laser system in order to distend either a knee joint or a shoulder joint during arthroscopic surgery.

In accordance with the preferred embodiment of the present invention a gas insufflation apparatus is described. The gas insufflation apparatus is used with an arthroscopic attachment having a gas inlet. A cylinder contains gas at a high pressure. A single stage regulator is fluidly coupled to the cylinder in order to regulate the inlet pressure of the gas. The gas insufflation apparatus includes a filter, an inlet relief valve and an inlet pressure gauge. The filter is fluidly coupled to the single stage regulator. The inlet relief valve insures that the inlet pressure of the gas does not exceed a predetermined pressure. The inlet pressure gauge reads the inlet pressure. The gas insufflation apparatus also includes a control valve and a flow meter. The control valve turns the flow of the gas through the gas insufflation apparatus on and off. The flow meter measures the flow of the gas through the gas insufflation apparatus. The gas insufflation apparatus further includes a first regulator and a second regulator. The first regulator insufflates the gas directly into the knee joint at a first preselected pressure in order to distend the knee joint during arthroscopic surgery. The second regulator insufflates the gas directly into the arthrosocpic attachment through the gas inlet at a second preselected pressure which is slightly higher than the first preselected pressure in order to distend the knee joint and provide positive gas flow through the arthroscopic attachment during arthroscopic surgery by the laser system.

The features of the present invention which are believed to be novel are set forth with particularity in the appended claims.

Other claims and many of the attendant advantages will be more readily appreciated as the same becomes better understood by reference to the following detailed description and considered in connection with the accompanying drawing in which like reference symbols designate like parts throughout the figures.

DESCRIPTION OF THE PREFERRED EMBODIMENT

Figure 1:
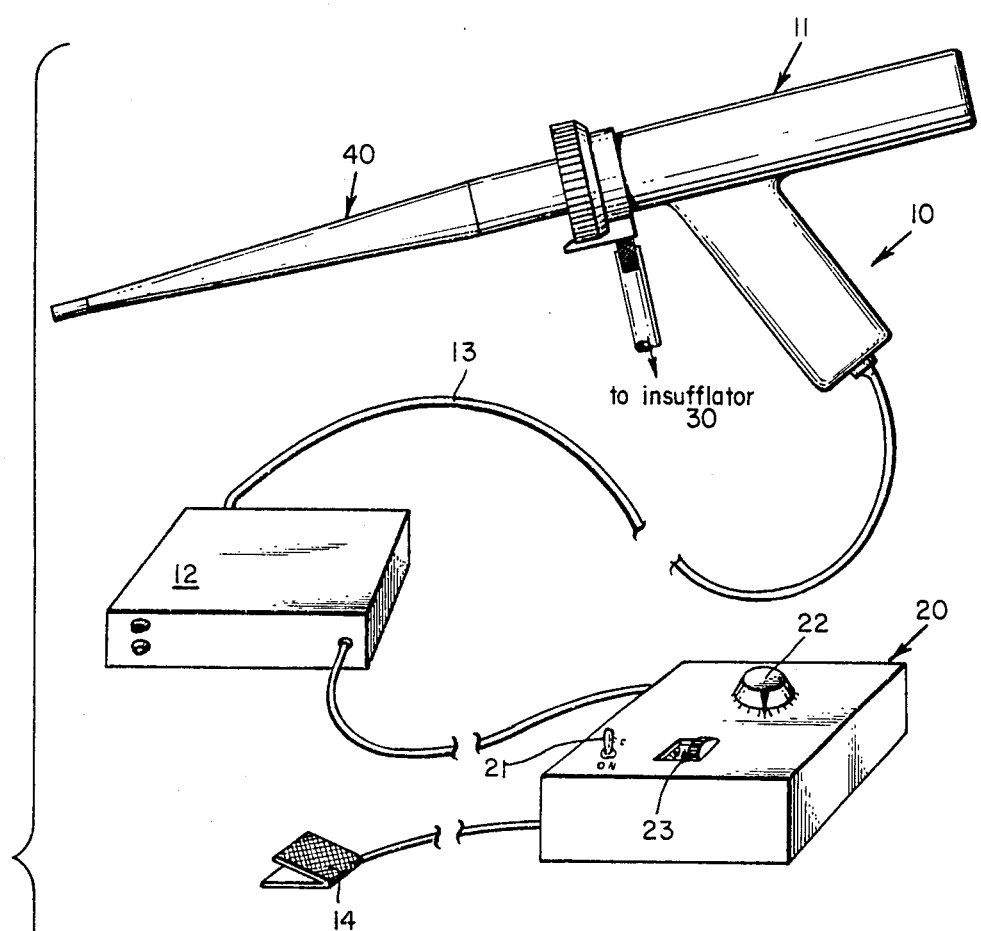
FIG. 1 is a perspective drawing of a hand held laser system and an arthroscopic attachment and a schematic drawing of a power supply, an electronic controller and a gas insufflation apparatus which has been constructed in accordance with the principles of the preferred embodiment of the present invention.
Figure 1:
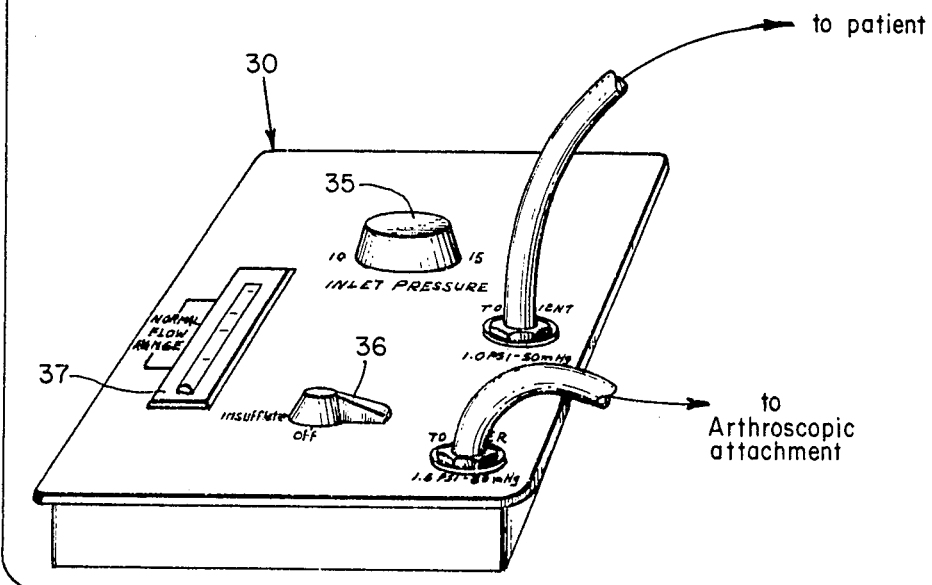

In order to best understand the present invention it is necessary to refer to the following description of its preferred embodiment in conjunction with the accompanying drawing. Referring to FIG. 1 a hand-held laser system 10 includes a laser output head 11, a power supply 12, and a connector 13 which electrically couples the power supply 12 to the laser output head 11. A foot switch 14 is electrically coupled to the power supply 12 through an electronic controller 20 which may be used in combination with the hand-held laser system 10 to control the duration of each output beam of light energy from the hand-held laser system 10 within a range of 0.005 seconds to 0.100 seconds and to limit the maximum number of pulses to a number which a surgeon may select for use in surgical procedures. The electronic controller 20 has an on/off switch 21, a pulse width setting switch 22 and a selector switch 23 for selecting the number of pulses. An orthopedic surgeon uses the hand-held laser system 10 to perform surgery under arthroscopic control. U.S. Pat. No. 4,369,768 teaches an arthroscope.

Figure 2:
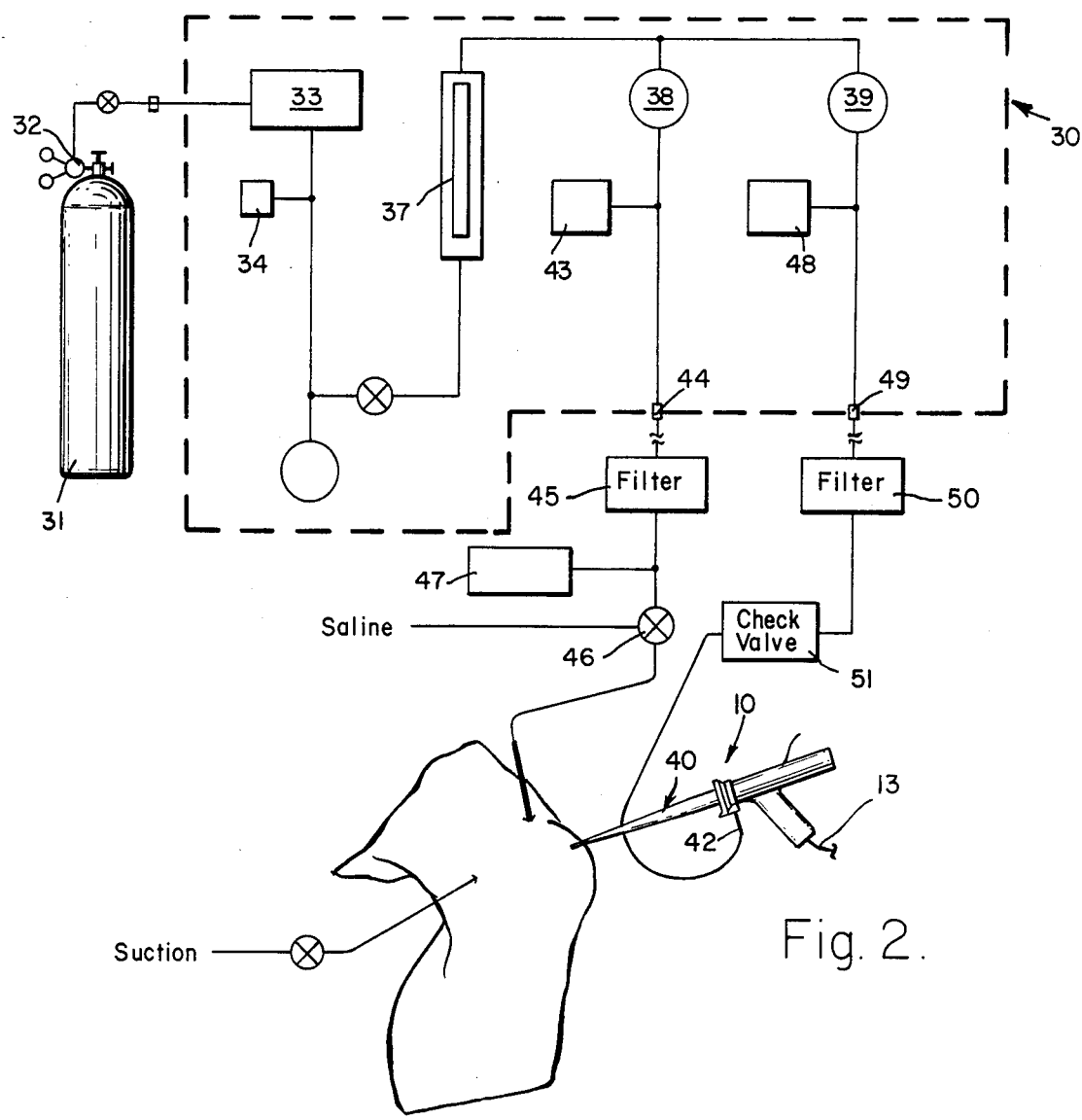
FIG. 2 is a schematic of the gas insufflation apparatus of FIG. 1.

Referring to FIG. 2 in conjunction with FIG. 1 a gas insufflation apparatus is used to distend the knee joint during arthroscopic surgery. A cylinder contains 31 gas at a high pressure. A single stage regulator 32 is fluidly coupled to the cylinder 31 in order to regulate the inlet pressure of the gas. The gas insufflation apparatus 30 includes a filter 33, an inlet relief valve 34 and an inlet pressure gauge 35. The filter 33 is fluidly coupled to the single stage regulator 32. The inlet relief valve 34 insures that the inlet pressure of the gas does not exceed a predetermined pressure. The inlet pressure gauge 35 reads the inlet pressure. The gas insufflation apparatus 30 also includes a control valve 36 and a flow meter 37. The control valve 36 turns the flow of the gas through the gas insufflation apparatus 30 on and off. The flow meter 37 measures the flow of the gas through the gas insufflation apparatus 30. The gas insufflation apparatus 30 further includes a first regulator 38 and a second regulator 39. The first regulator 38 insufflates the gas directly into the knee joint at a first preselected pressure in order to distend the knee joint during arthroscopic surgery. The gas insufflation apparatus 30 is used with an arthroscopic attachment 40 having an optical coupler 41 with a gas inlet 42. The second regulator 39 insufflates the gas directly into the arthroscopic attachment 40 through the gas inlet 42 at a second preselected pressure which is slightly higher than the first preselected pressure in order to provide positive gas flow through the arthroscopic attachment 40 into the knee joint.

Referring still to FIG. 2 the gas insufflation apparatus 30 still further includes a first relief valve 43 which is fluidly coupled to the first regulator 38, a first gas outlet 44 which is fluidly coupled to the first relief valve 43, a first microbacterial filter 45 which is fluidly coupled to the first gas outlet 44, a three-position control valve 46, which fluidly couples either a saline source or the gas through the first microbacterial filter 45 to the knee joint of a patient and which has an off-position, an on-position for saline and an on-position for gas, and an external relief valve 47 which is fluidly coupled to both the first microbacterial filter 45 and the three-position control valve 46. The gas insufflation apparatus 30 further yet includes a second relief valve 48 which is fluidly coupled to the second regulator 39, a second gas outlet 49 which is fluidly coupled to the second relief valve 48, a second external filter 50 which is fluidly coupled to the second gas outlet 49, a check valve 51 which fluidly couples the gas through the second microbacterial filter 50 to the gas inlet 42 of the arthroscopic attachment 40.

From the foregoing it can be seen that a gas insufflation apparatus for use with an arthroscopic attachment of a hand-held $CO_2$ laser system in order to distend a knee joint during laser arthroscopic surgery has been described. It should be noted that distances of and between the figures are not to be considered significant.

Accordingly it is intended that the foregoing disclosure and showing made in the drawing shall be considered only as an illustration of the principles of the present invention.

What is claimed is:

1. A combination of an arthroscopic attachment and a gas insufflation apparatus for use with a cylinder containing a gas at high pressure and a single stage regulator which is fluidly and mechanically coupled to the cylinder and which regulates the inlet pressure of the gas, said combination comprising:
   a. a filter which is fluidly coupled to the single stage regulator;
   b. an inlet relief valve which is fluidly coupled to said filter and which insures that the inlet pressure of the gas does not exceed a predetermined pressure;
   c. an inlet pressure gauge which is fluidly coupled to said filter and said inlet relief valve and which is used to read the inlet pressure;
   d. a control valve which is fluidly coupled to said filter and said inlet relief valve and which turns the flow of the gas through said gas insufflation apparatus on and off;
   e. a flow meter which is fluidly coupled to said control valve and which measures the flow of the gas through said gas insufflation apparatus; and
   f. a first regulator which has a first outlet relief valve and which is fluidly coupled to said flow meter;
   g. a hollow guide member which directs a beam of light energy from a laser system to a surgical target wherein said hollow guide member has an output tip;
   h. coupling means for optically coupling said beam of light to said guiding means, said coupling means being mechanically coupled to said hollow guide member;
   i. focusing means for focusing said beam of light energy so that the diameter of said focused beam of light energy is less than 0.8 millimeters at said output tip of said hollow guide member, said focusing means being optically and mechanically coupled to said coupling means;
   j. gas inletting means for letting a gas into said hollow guide member, said gas inletting means being mechanically coupled to said coupling means; and
   k. a second regulator which has a second outlet relief valve and which is fluidly coupled to said flow meter in order to insufflate the gas directly into said hollow guide member through said gas inletting means at a second preselected pressure which is slightly higher than said first preselected pressure in order to insufflate the gas directly into the knee joint at a first preselected pressure in order to distend the knee joint during arthroscopic surgery.

* * * * *